US00PP31747P3

(12) United States Plant Patent
Davasse

(10) Patent No.: US PP31,747 P3
(45) Date of Patent: May 12, 2020

(54) ***SPIRAEA* PLANT NAMED 'DAVROU01'**

(50) Latin Name: *Spiraea bumalda*
Varietal Denomination: DAVROU01

(71) Applicant: Jean-Paul Davasse, Angers (FR)

(72) Inventor: Jean-Paul Davasse, Angers (FR)

( * ) Notice: Subject to any disclaimer, the term of this patent is extended or adjusted under 35 U.S.C. 154(b) by 0 days.

(21) Appl. No.: 16/350,495

(22) Filed: Nov. 19, 2018

(65) Prior Publication Data

US 2019/0230833 P1 Jul. 25, 2019

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
CPC ... A01H 5/02; A01H 5/00; A01H 5/12; A01H 6/74; A01H 6/00
See application file for complete search history.

(56) References Cited

PUBLICATIONS

Floral Daily Part 3 Novelties at Plantarium 2017, retrieved on Sep. 3, 2019, retrieved from the Internet at https://www.floraldaily.com/article/9011274/novelties-at-plantarium-2017/, pp. 1,21-22. (Year: 2017).*

Kluepfel et al. Clemson Cooperative Extension Home & Garden Information Center *Spirea* Factsheet HGIC 1074 updated 2019, retrieved on Sep. 3, 2019, retrieved from the Internet at https://hgic.clemson.edu/factsheet/spirea/, 4 pp. (Year: 2019).*

Upov Pluto Plant Variety Database 20200129, retrieved on Feb. 5, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Cassandra Bright

(57) ABSTRACT

'DAVROU01' is a new cultivar of hybrid *Spiraea* with distinctive dark red-purple new foliage and stems. Plants are compact and bloom continuously throughout Spring and Summer. The new variety is a *Spiraea* normally produced as an outdoor garden or container plant.

3 Drawing Sheets

Latin name of the genus and species: *Spiraea bumalda.*

BACKGROUND OF THE INVENTION

The present invention comprises a new and distinct hybrid *Spiraea* cultivar hereinafter referred to by the cultivar name 'DAVROU01'. This new *Spiraea* was developed through a breeding program in Angers, France. 'DAVROU01' was selected from a population of seedlings grown from a controlled cross of *Spiraea* 'Denistar', U.S. Plant Pat. No. 22,432 as the seed parent and *Spiraea bumalda* 'Bailcarol', unpatented, as the pollen parent. The first asexual propagation of 'DAVROU01' was carried out in July 2014 by rooting stem cuttings at a research nursery in Angers, France, and has been asexually reproduced repeatedly by vegetative cuttings over a 5-year period. 'DAVROU01' has been found to retain its distinctive characteristics through successive asexual propagations.

SUMMARY OF THE INVENTION

The following are the unique combination of characteristics of this new cultivar when grown under standard horticultural practices at a research greenhouse in Angers, France.

1. Very compact plants.
2. Dark red-purple new foliage and stems.
3. Some resistance to powdery mildew.

COMPARISON TO PARENTAL VARIETIES

'DAVROU01' is similar to its female parent in most horticultural characteristics, however, the new variety differs in the following:

1. Coloration of the new foliage of 'DAVROU01' is greyed-purple, coloration of the new foliage of 'DENISTAR' is red to greyed-red.
2. Mature foliage color of the new variety is darker green than mature foliage color of the seed parent.
3. Flowering stems of the new variety are a darker red than flowering stems of the seed parent.

'DAVROU01' is similar to its male parent in most horticultural characteristics, however, the new variety differs in the following:

1. Coloration of the new foliage of 'DAVROU01' is greyed-purple, coloration of the new foliage of 'BAILCAROL' is light red.
2. Mature foliage color of the new variety is dark green, mature foliage color of the pollen parent is yellow-green.
3. Flower color of the new variety is darker pink than flower color of the pollen parent.

COMPARISON WITH COMMERCIAL CULTIVARS

'DAVROU01' can be compared to the commercial variety *Spiraea* 'Anthony Waterer', unpatented. The two *Spiraeas* are similar in most horticultural characteristics. The new variety, however differs in the following:

1. The new variety is more compact, approximately 50% smaller than 'Anthony Waterer'.
2. Mature foliage color of the new variety is darker green than that of 'Anthony waterer'.
3. Coloration of the new foliage of 'DAVROU01' is greyed-purple, coloration of the new foliage of 'Anthony Waterer' is light greyed-red.

BRIEF DESCRIPTION OF THE DRAWINGS

This new *Spiraea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Spiraea*.

DETAILED BOTANICAL DESCRIPTION

Figure 1:
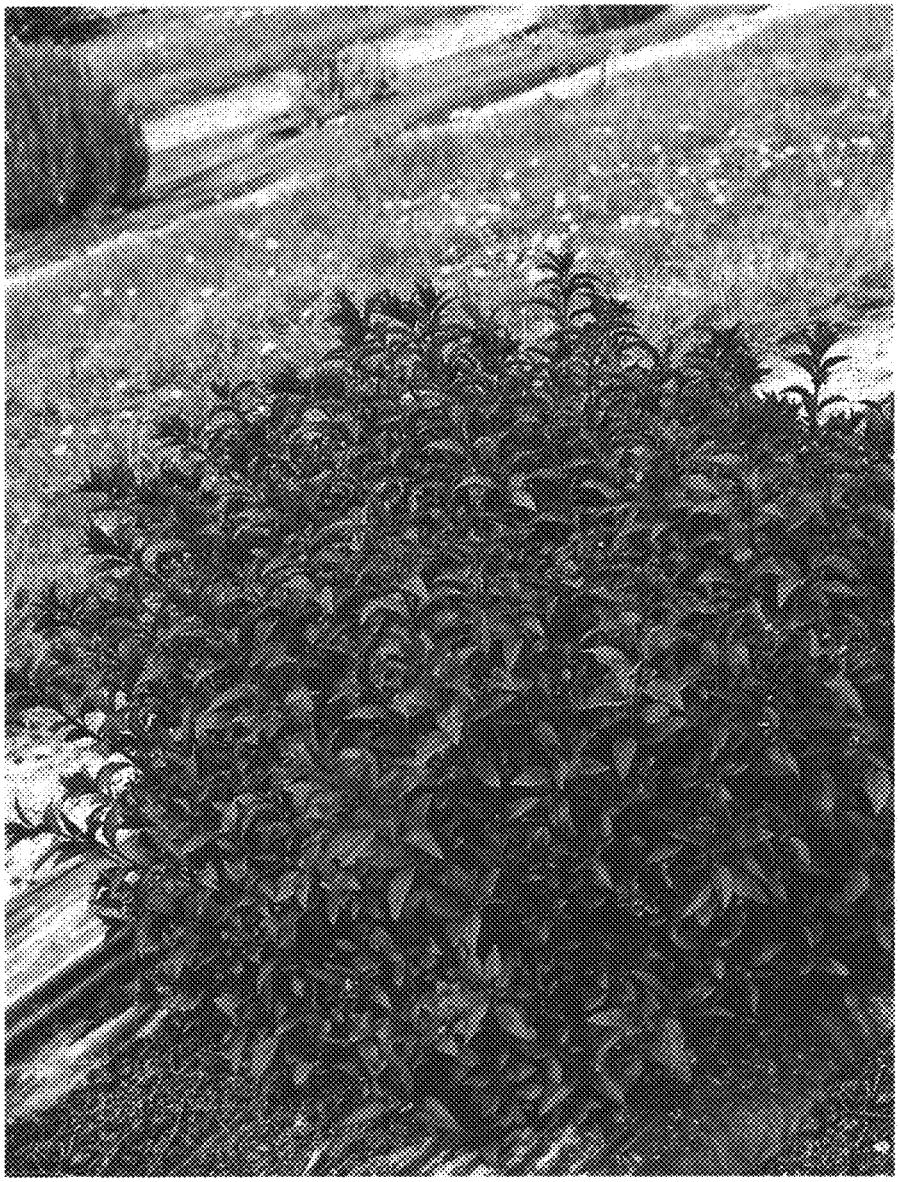
FIG. 1 is a color photograph showing the emerging foliage of 'DAVROU01' in Angers, France. The plant is approximately 2.5 years old, planted in the ground.
Figure 2:
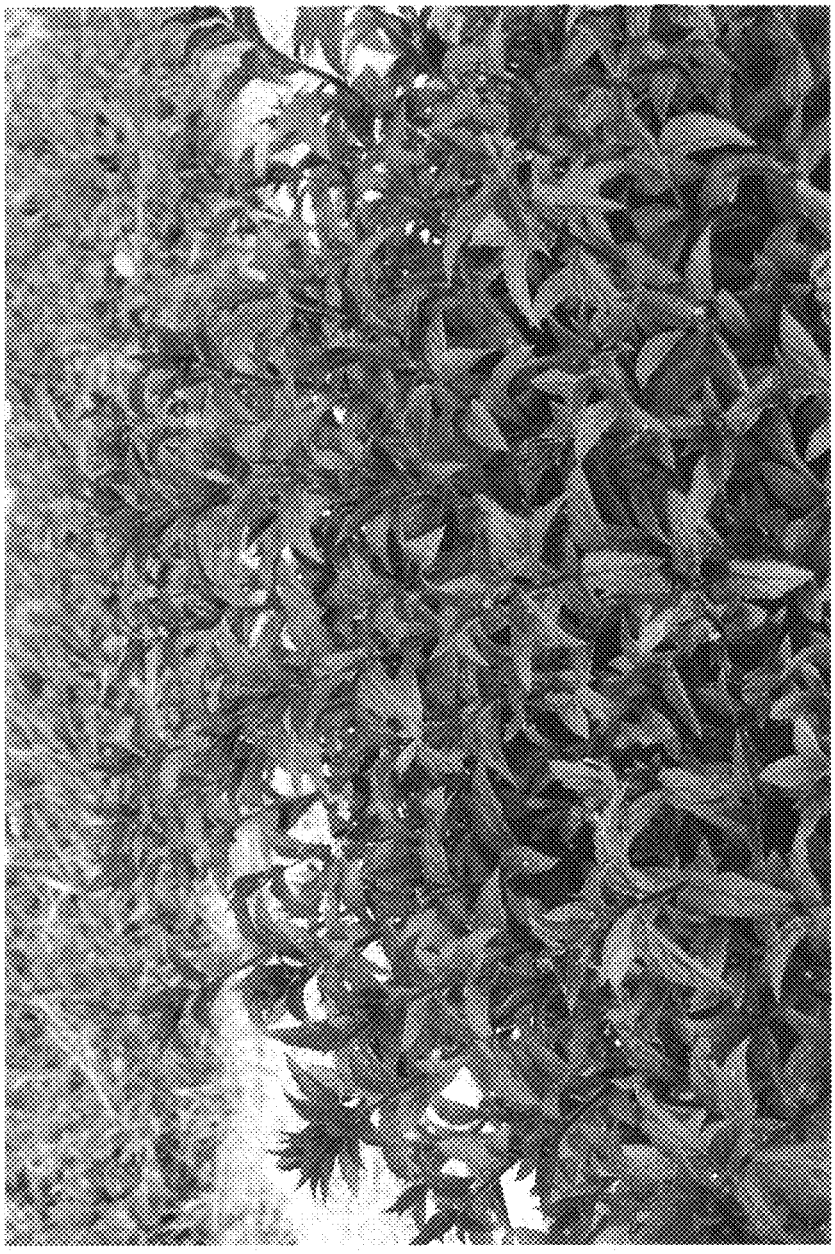
FIG. 2 is a close-up view of the emerging foliage of the same plant as FIG. 1.
Figure 3:
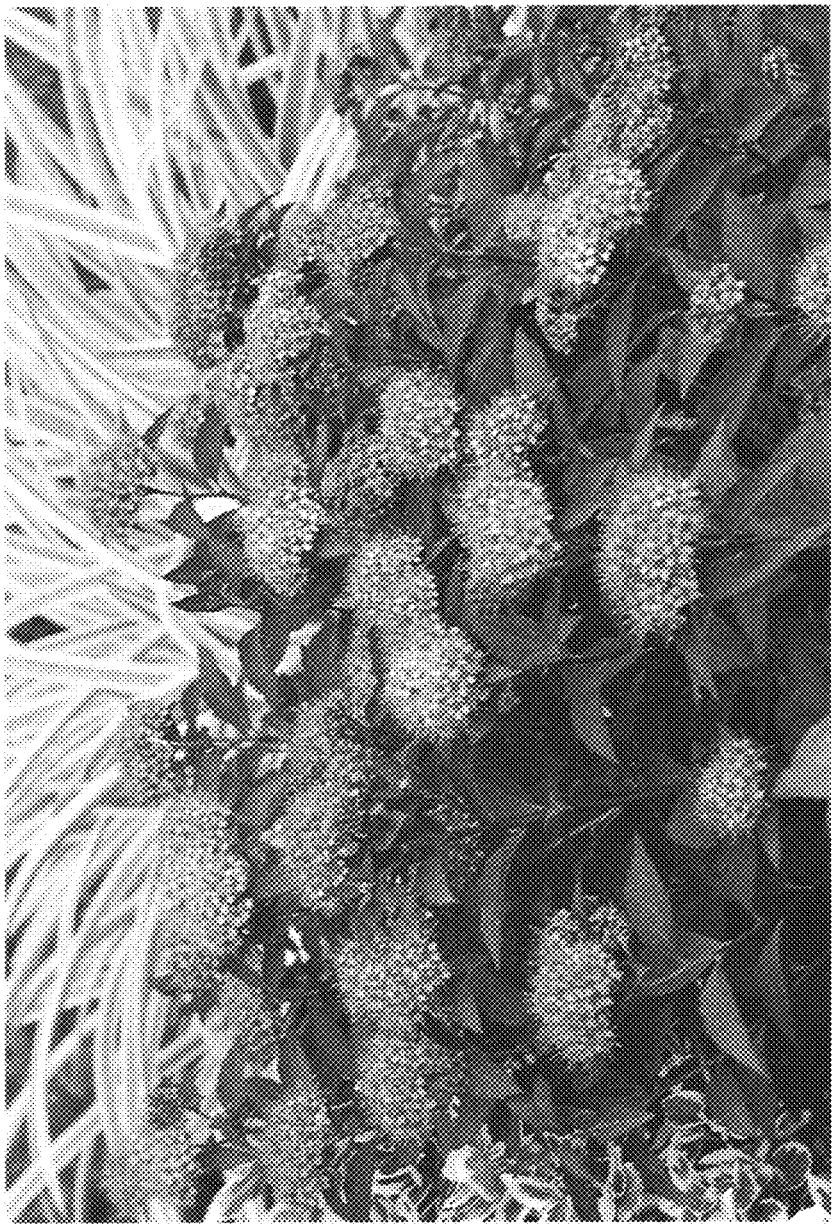
FIG. 3 is a color photograph showing a inflorescences and mature foliage of 'DAVROU01' in Angers, France.

The following is a detailed description of the botanical characteristics of the new and distinct hybrid *Spiraea* known by the denomination 'DAVROU01'. The detailed description was taken on a three-year-old field-grown plant in Angers, France. All colors cited herein refer to The Royal Horticultural Society Colour Chart (The Royal Horticultural Society (R.H.S.), London, 2007 Edition. Where specific dimensions, sizes, colors, and other characteristics are given, it is to be understood that such characteristics are approximations or averages set forth as accurately as practicable.

Classification:

*Botanical name.*—*Spiraea bumalda* 'DAVROU01'.

Plant description:

*Habit.*—Rounded/mounded woody deciduous shrub.

*Height.*—About 60 cm.

*Width.*—About 80 cm.

Branches: Average 4 per main stem.

*Lateral branch diameter.*—1 to 1.4 cm.

*Lateral branch length.*—30 to 50 cm.

*Internode length.*—1 to 2 cm.

*Branch color.*—Immature: Red-Purple 59A. Mature: Greyed-Purple 183A.

*Branch texture.*—Finely striated.

Leaves:

*Type.*—Simple.

*Persistence.*—Deciduous.

*Arrangement.*—Alternate.

*Shape.*—Ovate.

*Apex.*—Acute.

*Base.*—Acute.

*Venation.*—Pinnate.

*Vein color.*—Emerging leaves, upper and lower: Red-Purple 59A. Mature leaves: Upper surface Green 133B, lower surface 133B.

*Margins.*—Serrate.

*Color.*—Emerging leaves, upper and lower: Red-Purple 59A. Mature leaves: Upper surface Green 137A, lower surface 133B. Texture: Glabrous, both surfaces. Length of lamina: 5.0-6.5 cm. Width: 2.3-3.4 cm.

*Leaf attachment.*—Petiolate.

*Petiole.*—Length: 0.2 cm. Diameter: less than 0.1 cm. Color: Emerging leaves: Red-Purple 59A. Mature leaves: Green 133B. Texture: Glabrous.

Inflorescence:

*Description.*—Single whorled, rotate flowers arranged on a terminal corymb.

*Number of flowers per inflorescence.*—About 200.

*Flowering season.*—Spring and Summer in Angers, France.

*Inflorescence diameter.*—6-8 cm.

*Inflorescence height.*—About 4 cm.

*Bud.*—Shape: Globular. Length: about 2 mm. Diameter: about 2 mm. Color: Red-Purple 64C.

*Flower.*—Diameter: about 5 to 7 mm. Height: About 2 mm. Flower aspect: Upward and outwardly facing.

*Petal.*—Arrangement: Whorl. Number: 5. Fused: Not fused. Texture: Glabrous, all surfaces. Shape: Orbicular. Margin: Entire. Apex: Obtuse. Base: Obtuse. Length: 2 to 3 mm. Width: about 2 mm. Color when opening: Red-Purple 64C. Color at anthesis: Red-Purple 64C, fading to Red-Purple 65D in center.

*Calyx.*—Shape: Cup-shaped with five lobes. Length: About 3 mm. Diameter: About 2 mm.

*Sepal.*—Arrangement: Single whorl. Number: 5. Texture: Pubescent along margins. Shape: Acute. Margin: Entire. Apex: Acute. Base: Fused. Color: Near Green 133B, both surfaces. Length: About 1.3 mm. Width: About 0.7 mm.

*Peduncle.*—Length: About 1.5 to 3.5 mm. Diameter: About 8 to 10 mm. Color: Near Red-Purple 59A. Texture: Pubescent.

*Pedicels.*—Length: 3 to 5 mm. Diameter: About 1 mm. Color: Near Red-Purple 59B. Texture: Glabrous to lightly pubescent.

Reproductive organs:

*Gynoecium.*—Pistil number: 5. Pistil length: 3 mm. Stigma shape: linear. Stigma color: Near Red-Purple 59A. Style length: 2 mm. Style color: Near Red-Purple 59B. Ovary color: Near Yellow-Green 144C.

*Androecium.*—Stamen number: 10 to 20. Anther shape: Linear. Anther size: 2 mm. Anther color: Near Red-Purple 59C. Filament length: 4 to 6 mm. Filament color: Near Red-Purple 59D. Amount of pollen: Moderate. Pollen color: White 155C.

Other:

*Fruit and seed.*—Not observed to date.

Disease and insect resistance: Some tolerance for powdery mildew observed. Neither resistance nor susceptibility to other normal diseases and pests has been observed.

Temperature tolerance: USDA Zones 4 to 8. Cold hardy to at least −25° C.

What is claimed is:

1. A new and distinct hybrid *Spiraea* plant named 'DAVROU01' substantially as illustrated and described herein.

* * * * *